United States Patent
Yamashita et al.

(10) Patent No.: US 12,251,498 B2
(45) Date of Patent: Mar. 18, 2025

(54) IMPLANT FOR NON-LUMINAL AREA

(71) Applicant: Japan Medical Device Technology Co., Ltd., Kumamoto (JP)

(72) Inventors: Shuzo Yamashita, Kumamoto (JP); Makoto Sasaki, Kumamoto (JP); Akira Wada, Kumamoto (JP)

(73) Assignee: Japan Medical Device Technology Co., Ltd., Kumamoto (JP)

( * ) Notice: Subject to any disclaimer, the term of this patent is extended or adjusted under 35 U.S.C. 154(b) by 595 days.

(21) Appl. No.: 17/486,150

(22) Filed: Sep. 27, 2021

(65) Prior Publication Data

US 2022/0008625 A1 Jan. 13, 2022

Related U.S. Application Data

(63) Continuation of application No. PCT/JP2020/013768, filed on Mar. 26, 2020.

(30) Foreign Application Priority Data

Mar. 28, 2019 (JP) .................................. 2019-062874
Jan. 8, 2020 (JP) .................................. 2020-001520

(51) Int. Cl.
*A61L 27/58* (2006.01)
*A61L 27/04* (2006.01)
(Continued)

(52) U.S. Cl.
CPC ............. *A61L 27/58* (2013.01); *A61L 27/047* (2013.01); *A61L 27/306* (2013.01); *C22C 23/04* (2013.01);
(Continued)

(58) Field of Classification Search
CPC ...... A61L 27/58; A61L 27/047; A61L 27/306; A61L 2420/02; A61L 2430/02;
(Continued)

(56) References Cited

U.S. PATENT DOCUMENTS 9,402,669 B2 8/2016 Neubert et al.
9,504,554 B2 11/2016 Bayer et al.
(Continued)

FOREIGN PATENT DOCUMENTS

CN 103826668 A 5/2014
CN 104784750 A 7/2015
(Continued)

OTHER PUBLICATIONS

International Search Report, and English Translation thereof, for International Application No. PCT/JP2020/013768, mailed May 12, 2020, (6 pages).

(Continued)

*Primary Examiner* — Jerrah Edwards
*Assistant Examiner* — Jose H. Trevino, III
(74) *Attorney, Agent, or Firm* — Kagan Binder, PLLC (57) ABSTRACT

A bioabsorbable implant for non-luminal region comprising: a core structure including a magnesium alloy having a predetermined shape; a first corrosion-resistant layer containing a magnesium fluoride layer as a main component formed on the core structure via fluorination of a surface of the magnesium alloy; and a second corrosion-resistant layer containing a parylene formed on the magnesium fluoride layer.

10 Claims, 1 Drawing Sheet

(51) Int. Cl.
*A61L 27/30* (2006.01)
*C22C 23/04* (2006.01)
*C23C 28/00* (2006.01)

(52) U.S. Cl.
CPC ........... *C23C 28/00* (2013.01); *A61L 2420/02* (2013.01); *A61L 2430/02* (2013.01); *A61L 2430/12* (2013.01)

(58) Field of Classification Search
CPC ........... A61L 2430/12; A61L 2300/608; A61L 31/022; A61L 31/088; A61L 31/10; A61L 31/148; C22C 23/04; C23C 28/00; C23C 22/34; B05D 2202/20; B05D 2350/60; B05D 1/60; C25F 3/18
See application file for complete search history.

(56) References Cited

U.S. PATENT DOCUMENTS

| | | | |
|---|---|---|---|
| 2014/0199365 | A1 | 7/2014 | Stekker et al. |
| 2014/0200652 | A1* | 7/2014 | Bayer ................. C23G 1/12 420/407 |
| 2014/0277396 | A1 | 9/2014 | Mendelson et al. |
| 2015/0080998 | A1* | 3/2015 | Mueller ............. A61L 27/58 623/1.1 |
| 2019/0024244 | A1 | 1/2019 | Lee et al. |
| 2019/0330718 | A1 | 10/2019 | Ueda et al. |
| 2019/0343666 | A1 | 11/2019 | Sasaki et al. |
| 2020/0001013 | A1 | 1/2020 | Holmqvist |
| 2020/0139017 | A1* | 5/2020 | Meyer-Kobbe ....... A61L 31/028 |
| 2021/0001013 | A1* | 1/2021 | Sasaki .................. A61L 31/16 |
| 2021/0115539 | A1 | 4/2021 | Ueda et al. |
| 2021/0353836 | A1* | 11/2021 | Yamashita .............. A61F 2/915 |
| 2022/0033974 | A1* | 2/2022 | Yamashita ............ A61L 27/303 |

FOREIGN PATENT DOCUMENTS

| | | |
|---|---|---|
| CN | 105256213 A | 1/2016 |
| JP | 2014533967 A | 12/2014 |
| WO | 2018122418 A1 | 7/2018 |
| WO | 2018131476 A1 | 7/2018 |
| WO | 2018139647 A1 | 8/2018 |
| WO | 2019182003 A1 | 9/2019 |
| WO | 2020012529 A1 | 1/2020 |

OTHER PUBLICATIONS

Liu et al., "Multifunctional MgF2/polydopamine coating on Mg alloy for vascular stent application", Journal of Materials Science and Technology, vol. 31, pp. 733-743, 2015, (11 pages).
JP Patent Search Machine Translation for JP2014533967A.
English Abstract for WO2018139647A1. Espacenet.
English Abstract for WO2018131476A1. Espacenet.
English Abstract for WO2019182003A1. Espacenet.
English Abstract for WO2020012529A1. Espacenet.
Extended European Search Report for European Application No. 20777976.0, mailed Mar. 13, 2023, (8 pages).
Decision of Refusal, and English Translation therefore, for Chinese Application No. 202080025410.5, mailed Mar. 13. 2023, (21 pages).
Ma Chengxun, "Precision forging technology for intelligent manufacturing", 7th National Precision Forging Society Papers, Hefei University of Technology Press, pp. 295-299, Jun. 30, 2018, (15 pages). (English language machine Translation generated by "Google Translate").
Chinese Office Action for Chinese Application No. 202080025410. 5, mailed Feb. 11, 2022, (18 pages).
Kun, "China magnesium industry progress," Metallurgical Industry Press, pp. 127-131, 2012, (14 pages). (English Translation).
E-Space English Abstract and machine Translation for CN 103826668 A.
E-Space English Abstract and machine Translation for CN 104784750 A.
E-Space English Abstract and machine Translation for CN 105256213 A.
E-Space English Abstract and machine Translation for WO 2018122418 A1.
International Preliminary Report on Patentability for International Application No. PCT/JP2020/013768, mailed Oct. 7, 2021, (9 pages).
Second Chinese Office Action, and English Translation therefore, for Chinese Application No. 202080025410.5, mailed Jul. 5, 2022, (19 pages).

\* cited by examiner

IMPLANT FOR NON-LUMINAL AREA

CROSS REFERENCE TO THE RELATED APPLICATION

This application is a continuation application, under 35 U.S.C § 111(a) of international application No. PCT/JP2020/013768, filed Mar. 26, 2020, which claims priority to Japanese patent applications No. 2019-062874 filed Mar. 28, 2019 and No. 2020-001520 filed Jan. 8, 2020, the entire disclosures of which are herein incorporated by reference as a part of this application.

FIELD OF THE INVENTION

The present invention relates to an implant for non-luminal region made of a biodegradable magnesium alloy in which the surface of the magnesium alloy is modified by covering the surface of the magnesium alloy with a corrosion inhibitory layer.

The implant for non-luminal region according to the present invention can be used as an implant for orthopedic surgery, oral surgical surgery, plastic surgery, cerebral surgery, and others.

BACKGROUND OF THE INVENTION

In modern medical technology, implants are widely applied as supports for surgical purposes, such as for attachment or fixation of tissues or bones. However, the implants remaining in the human body after given treatment would induce various complications in the human body. Accordingly, there is an inconvenience such that the inserted implant must be removed from the human body through additional treatment after achieving the purposes of the implant.

Many studies have been done to produce implants from biodegradable materials as implant metals, and as a result, biodegradable materials consisting of a variety of materials such as polymer-based materials, ceramic-based materials, and metal-based materials have been proposed.

In response to this, the development of metal materials having biodegradability as well as strength, processability and ductility has been eagerly desired, and magnesium, iron, tungsten, and the like have been proposed as biodegradable materials. Of these materials, magnesium has been particularly attracting attention as the most suitable biodegradable material, and recently, magnesium alloys have begun to be used for some fixing screws and the like for bonding bones.

The rate of biodegradation of biodegradable materials in vivo must proceed in proportion to the rate of tissue regeneration. Where the degradation rate of the magnesium alloy is too fast, the magnesium alloy will lose stability before recovery of the damaged tissues, resulting in failure of basic function as the medical instrument. On the contrary, if the degradation rate of the magnesium alloy is too slow, it would result in a higher risk such as complication. Therefore, the control of the degradation rate of biodegradable magnesium corresponds to an essential factor to be considered in the design of medical instruments using biodegradable magnesium. Therefore, as a surface treatment of the biodegradable magnesium alloy, an attempt has been made to treat the surface of the magnesium alloy with an aqueous hydrofluoric acid solution (fluoric acid treatment) (Patent Document 1, etc.).

CONVENTIONAL ART DOCUMENT

Patent Document

[Patent Document 1] WO 2018/139647

SUMMARY OF THE INVENTION

Problems to be Solved by the Invention

The present inventors have found that, in order to appropriately control the degradation rate of the surface of the magnesium alloy, it is not sufficient just to form a magnesium fluoride layer on the surface of the magnesium alloy by treating the surface of the magnesium alloy with magnesium fluoride as described in the above-mentioned conventional art document.

Therefore, the problem to be solved by the present invention is to form a magnesium fluoride layer on the surface of the magnesium alloy, and further suppress the degradation rate of the magnesium alloy covered with the magnesium fluoride layer by means of forming a corrosion-resistant layer on the magnesium fluoride layer. In such a manner, a non-luminal implant made of a magnesium alloy covered with such a corrosion-resistant layer can be obtained.

As a result of intensive studies on the above problems, the present inventors have found that degradation rate of the surface of the magnesium alloy can be appropriately controlled by forming a magnesium fluoride layer (first layer) on the surface of the magnesium alloy by means of giving fluorinated treatment on the surface of the magnesium alloy, and further forming a parylene layer (second layer) on the surface of the magnesium fluoride layer, whereby a practical implant for non-luminal region can be obtained. In such a manner, the inventors of the present invention have reached the present invention.

Means to Solve Problems

The present invention comprises the following aspects.
Aspect 1
A bioabsorbable implant for non-luminal region comprising:
  a core structure comprising a magnesium alloy having a predetermined shape;
  a first corrosion-resistant layer containing a magnesium fluoride layer as a main component formed on the core structure via fluorination of a surface of the magnesium alloy; and
  a second corrosion-resistant layer containing a parylene formed on the magnesium fluoride layer.

Biodegradation rate of magnesium can be controlled within a suitable range as an implant, where a magnesium alloy is used, the surface of the magnesium alloy is fluorinated to form a fluorinated layer, and further, a parylene layer is formed on the fluorinated layer.

In the present invention, the term "non-luminal region" refers to a region other than organism lumens (blood vessel, lymphatic vessel, ureter, etc.).

It is preferable that both the fluorinated layer and the parylene layer are formed over the entire surface of the magnesium alloy.
Aspect 2
  The implant for non-luminal region according to aspect 1, wherein the magnesium alloy comprises, in % by mass, 0.95 to 2.00% of zinc, equal to or higher than 0.05% and less than 0.30% of zirconium, 0.05 to 0.20% of manganese, and the balance consisting of magnesium and unavoidable impurities, with an average crystal grain size of 1.0 to 3.0 μm and a standard deviation of grain size distribution of 0.7 μm or less.

Since the implant for non-luminal region is used for the treatment of the human body and may be indwelled in the human body for a certain period of time, the magnesium alloy having the above constitution is preferably used from the viewpoint of safety to the human body. Among them, the magnesium alloy which has a total amount of unavoidable impurities of 30 ppm or less and does not contain rare elements and aluminum is preferable.

The above magnesium alloy may have a fracture elongation of 15 to 50% as measured by JIS Z2241. The fracture elongation preferably exceeds 30%.

The magnesium alloy may have a tensile strength of 250 to 300 MPa and a proof stress of 145 to 220 MPa as measured by JIS Z2241.

The magnesium alloy preferably does not contain a precipitate having a grain size of 500 nm or larger, and more preferably does not contain a precipitate having a grain size of 100 nm or larger.

Aspect 3

The implant for non-luminal region according to aspect 1 or 2, wherein the magnesium alloy has a wheel shape, a plate shape, a rod shape, a pipe shape, a band shape, a wire shape, a ring shape, or a combination of at least one shape as described above.

For non-luminal implants, magnesium alloys having the shape selected in accordance with the intended purpose are used.

Aspect 4

The implant for non-luminal region according to any one of aspects 1 to 3, wherein the implant for non-luminal region is for orthopedic use, oral surgical use, plastic surgical use, or cerebral surgical use.

Aspect 5

The implant for non-luminal region according to any one of aspects 1 to 4, wherein the implant for non-luminal region is used as (1) an implant for suture instruments such as a clip, a stapler, a wire, and a surgical needle, or (2) an implant as bone junction members such as a bone pin, a bone screw, and a suture anchor.

Aspect 6

The implant for non-luminal region according to any one of aspects 1 to 5, wherein the magnesium fluoride layer has a layer thickness of 0.5 to 1.5 μm.

In aspect 6, although a magnesium fluoride layer formed on the surface of the magnesium alloy is effective in reducing the degradation rate of the magnesium alloy, it may be difficult to form a magnesium fluoride layer in a thickness exceeding 1.5 μm. Accordingly, the thickness of the magnesium fluoride layer may be appropriately selected from the range of 0.5 to 1.5 μm.

Aspect 7

The implant for non-luminal region according to any one of aspects 1 to 6, wherein the parylene layer comprises a parylene N (chemical formula 1 below), a parylene C (chemical formula 2 below), a parylene M (chemical formula 3 below), a parylene F (chemical formula 4 below), a parylene D (chemical formula 5 below), or a parylene HT (chemical formula 6 below).

[Chem 1]

(1)

(2)

(3)

(4)

(5)

(6)

Aspect 8

The implant for non-luminal region according to any one of aspects 1 to 7, wherein the layer thickness of the parylene layer is 0.05 to 1 μm.

In this aspect, since a thin parylene layer is formed on the magnesium fluoride layer, it is possible to control the degradation rate of the magnesium alloy effectively with the thin parylene layer.

Aspect 9

The implant for non-luminal region according to any one of aspects 1 to 8, wherein a biomaterial layer comprising at least one biomaterial selected from the group consisting of a biodegradable polymer, a protein, and a calcium phosphate is formed on the surface of at least a part of the parylene layer.

Aspect 10

A method of producing a non-luminal implant comprising (1) a magnesium fluoride layer on a surface of a magnesium alloy and (2) a parylene layer on the magnesium fluoride layer, the method comprising:

(1) subjecting a surface of a magnesium alloy having a predetermined shape to fluorination treatment to form a magnesium fluoride layer on the surface of the magnesium alloy, and (2) subjecting the magnesium fluoride layer to vapor deposition coating of poly-para-xylylene resin to form a parylene layer.

As mentioned above, the magnesium alloy may have a wheel shape, a plate shape, a rod shape, a pipe shape, a band shape, a wire shape, a ring shape, or a combination of at least one shape as described the above. That is, the magnesium alloy may have various shapes depending on use. The variously shaped magnesium alloy is immersed into hydrofluoric acid solution so as to perform a fluorination treatment, and then, the parylene layer is formed on the fluorination treated layer. As such, the implant for non-luminal region according to the present invention can be produced.

Note that any combination of at least two components disclosed in the claims and/or the specification and/or the drawings is included in the present invention. In particular, any combination of two or more of the following claims is included in the present invention.

Effects of the Invention

According to the first aspect of the present invention, an implant for non-luminal region enables to have a corrosion resistance, as well as to maintain the mechanical strength for a predetermined period of time, in which the implant is obtained by forming a magnesium fluoride layer on the surface of a magnesium alloy and then forming a parylene layer on the magnesium fluoride layer.

Since the parylene layer is further formed on the magnesium fluoride layer, is provided a non-luminal implant having sufficient corrosion resistance for various applications.

The magnesium fluoride layer is biodegraded and absorbed into the body, but the parylene layer is not absorbed into the body. By forming the parylene layer on the magnesium fluoride layer, it is possible to make the parylene layer thinner, and as a result, the influence of the remaining parylene layer on the body can be reduced.

As illustrated in Comparative Examples 1 and 2 shown below, single use of parylene exhibit less suppressive elution of magnesium alloy than single use of magnesium fluoride. Unexpectedly, by combining a magnesium fluoride layer and a parylene layer, the combination of these layers achieves improved corrosion resistance as compared with single use of magnesium fluoride. That is, where the first anticorrosion layer is covered with the second anticorrosion layer made of parylene layer, a synergistic effect such that the corrosion resistance of the first anticorrosion layer is maintained for a longer period of time can be obtained.

In the second aspect of the present invention, the magnesium alloy free from rare metals and aluminum is excellent in safeness to human bodies. The magnesium alloy may include an alloy composed of substantially single-phase solid solution or have a microstructure in which nanometer-sized fine Zr-bearing precipitates are dispersed in the single-phase alloy. The magnesium alloy has excellent deformability (ductility, elongation ability) because of its fine and uniform particle size and has excellent mechanical properties such as tensile strength and proof strength because of the absence of coarse precipitates at which a fracture starts.

Where the unavoidable impurities of the magnesium alloy include Fe, Ni, Co, and/or Cu, a content of each of Fe, Ni, Co, and Cu being preferably lower than 10 ppm. The magnesium alloy may preferably be free of Co as an unavoidable impurity.

The implant for non-luminal regions comprising the above magnesium alloy has excellent deformation characteristics and biodegradation characteristics of which are adequately controlled.

In the third aspect of the present invention, since both the first layer and the second layer formed on the surface of the magnesium alloy with an arbitrary shape have excellent deformation followability, the implant can be used for various purposes.

In the fourth and fifth aspects of the present invention, the non-luminal implant according to the present invention can be used for various therapeutic applications, and eventually, the magnesium alloy itself is decomposed and absorbed into the body tissue, while the parylene layer is closely attached to the body tissue and buried therein thanks to thin thickness.

In the sixth aspect of the present invention, although corrosion resistance is improved as the thickness of the magnesium fluoride layer becomes larger, it may be necessary to consider a balance between the deformation followability and thickness of the magnesium fluoride layer.

In the seventh and eighth aspects of the present invention, the magnesium alloy comprising the magnesium fluoride layer and the parylene layer formed on the magnesium fluoride layer are more effectively suppressing the decomposition rate of magnesium as compared with the magnesium alloy comprising only the magnesium fluoride layer. Of all parylene layers, a parylene layer formed from a parylene C is preferable in terms of deformation followability Although the thickness of the parylene layer can be selected in the range of 0.05 to 1 μm, it is preferable to minimize the thickness of the parylene layer because the parylene layer remains in the living body.

In the ninth aspect of the present invention, it is preferable that a biomaterial layer (such as a biodegradable polymer layer, a protein layer, and a calcium phosphate layer) is formed on the surface of at least a part of the parylene layer. The biomaterial layer plays a role on, for example, improving deliverability of a magnesium alloy product to a predetermined location in the living body, protecting the parylene layer from external stress, improving biocompatibility and functionality of the magnesium alloy products for living tissues, carrying medical agents (such as antiphlogistine, sedative drug, bone-building drug, limus-based drug), and others.

The biodegradable polymer may comprise two layers, an inner layer on the parylene layer side, and an outer layer on the living body side; and the drug may be contained in the inner layer, the outer layer, or both.

According to the tenth aspect of the present invention, the magnesium fluoride layer (first layer) is formed on the surface of the magnesium alloy with an arbitrary shape, and the parylene layer (second layer) is further formed on the magnesium fluoride layer. In such a manner, the non-luminal implant with the first layer and the second layer can be produced.

BRIEF EXPLANATION OF THE DRAWINGS

The present invention will be more clearly understood from the preferred embodiments described below with reference to the attached drawings. However, the embodiments and the drawings are merely illustrative and explanatory, and should not be used for defining the scope according to the present invention. The scope according to the present invention is defined by the attached claims.

DESCRIPTION OF THE EMBODIMENTS

Implant for Non-Luminal Region

Figure 1:
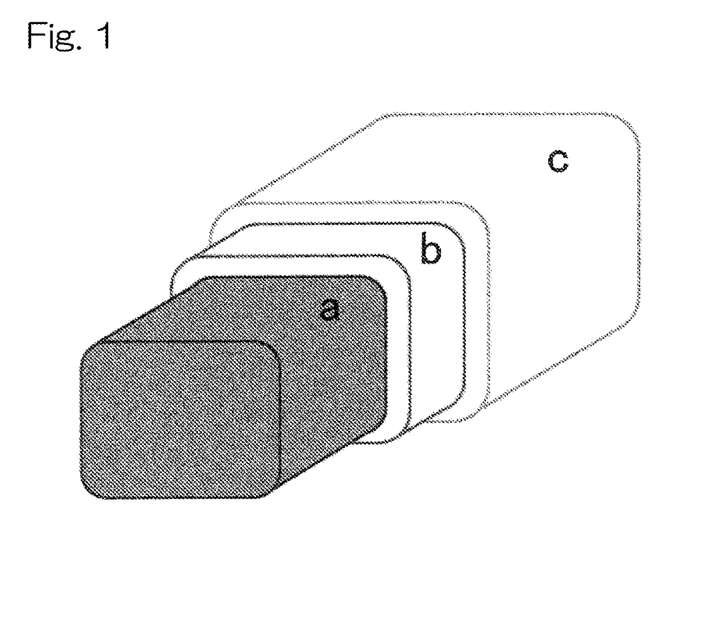
FIG. 1 is a schematic view illustrating components of an implant for a non-luminal region according to an embodiment of the present invention.

As shown in FIG. 1, an example of an implant (Mg alloy) for a non-luminal region according to the present invention includes: a magnesium alloy (a) having a predetermined shape; a magnesium fluoride ($MgF_2$) layer (first layer) (b) formed by subjecting the surface of the magnesium alloy (a) to fluorination treatment; and a parylene layer (second layer) (c) formed on the magnesium fluoride layer (b). The surface of the magnesium fluoride layer (b) includes $Mg(OH)_2$ and others formed by oxidation of Mg on the surface, and exhibits hydrophilic property.

As technical elements of the above configuration: there may be mentioned an element for selecting a magnesium alloy composition having biodegradability and adaptability depending on its use; an element for forming a magnesium fluoride layer mainly containing $MgF_2$ on the surface of the magnesium alloy so as to control the corrosion of the magnesium alloy having the selected alloy composition; and element for forming a carbon-coated layer (second layer) containing a parylene on the magnesium fluoride layer.

Magnesium Alloy

Magnesium alloys used in the present invention include AZ series (Mg—Al—Zn) (AZ31, AZ61, AZ91 and the like), AM series (Mg—Al—Mn), AE series (Mg—Al-RE), EZ series (Mg-RE-Zn), ZK series (Mg—Zn—Zr), WE series (Mg-RE-Zr), AX or AXJ series (Mg—Al—Ca) etc. Moreover, examples thereof may include magnesium alloys containing 90 mass % or more of magnesium, and zinc (Zn), zirconium (Zr), and manganese (Mn) as accessory components, which does not contain aluminum (Al) and rare metals (RE) that are harmful to the human body. The magnesium alloy used in the present invention preferably contains 90 mass % or more of magnesium (Mg) as a main component, zinc (Zn), zirconium (Zr), and manganese (Mn) as accessory components, and 30 ppm or less of unavoidable impurities selected from the group consisting of iron (Fe), nickel (Ni), cobalt (Co), and copper (Cu), and excluding aluminum and at least one sort of rare earths selected from the group consisting of scandium (Sc), yttrium (Y), dysprosium (Dy), samarium (Sm), cerium (Ce), gadolinium (Gd), and lanthanum (La). This specific composition secures safety to living body as well as mechanical properties.

From the viewpoint of enhancing living body safety and mechanical property, the content of Mg is preferably 93 mass % or more, and still more preferably 95 mass % or more. By not containing at least one sort of rare earths selected from the group consisting of Sc, Y, Dy, Sm, Ce, Gd, and La, and aluminum, preferably by not containing all of the above rare earths and Al, it is possible to prevent harm to the human body.

The preferred magnesium alloy according to the present invention includes, in % by mass, 0.95 to 2.00% of zinc, equal to or higher than 0.05% and less than 0.30% of zirconium, 0.05 to 020% of manganese, and the balance consists of magnesium and unavoidable impurities, with an average crystal grain size of 1.0 to 3.0 µm and a standard deviation of grain size distribution of 0.7 µm or less.

According to the present invention, benefit such as improvement in plastic workability can be achieved by controlling the composition of the magnesium alloy within the above range. Further, the characteristics such as fracture elongation are improved by refining/uniformizing the particle size of the alloy.

The magnesium alloy having the above composition can avoid formation of coarse precipitates which may be triggers (starting points) of fractures and thereby reduce the possibility of breakage during and after deformation. It should be noted that although Zr, which is added in order to reduce the crystal particle size of the alloy, may form precipitates, the precipitates are typically dispersed at a nanometer scale (in a size smaller than 100 nm) in the matrix phase and thus has a negligible impact on deformation and corrosion of the alloy.

Zinc (Zn): In % by Mass, 0.95% or More and 2.00% or Less

Zn is added to form a solid-solution with Mg and to enhance strength and elongation of the alloy. Where the amount of Zn is less than 0.95%, intended effect cannot be obtained. The amount of Zn more than 2.00% may be unpreferable, since Zn content may exceed the solid-solubility limit, resulting in non-desired formation of Zn-rich precipitates that reduce the corrosion resistance. Accordingly, the contained amount of Zn is set to 0.95% or more and 2.00% or less in the preferred magnesium alloy. However, the contained amount of Zn may be less than 2.00%.

Zirconium (Zr): In % by Mass, 0.05% or More and Less than 0.30%

Zr scarcely forms solid-solution with Mg, and forms fine-grained precipitates, thereby preventing coarsening of crystal grains of alloy. Where the amount of Zr is less than 0.05%, effects of Zr addition cannot be obtained. Where the amount of Zr is 0.30% or more, precipitates may be formed in a higher amount, thereby may reduce the effect on particle size refinement. Addition of Zr at an amount equal to or exceeding 0.30% leads to formation of a larger amount of precipitates, with a reduced effect of particle size reduction. In addition, corrosion and breakage would start occurring at portions where the precipitates are biased. For this reason, content of Zr is regulated to 0.05% or more and less than 0.30% in the preferred magnesium alloy. The content of Zr may be 0.10% or more and less than 0.30%.

Manganese (Mn): In % by Mass, 0.05% or More and 0.20% or Less

Mn has effects of refining grain size of the alloy and enhancing corrosion resistance of the alloy. Where the amount of Mn is less than 0.05%, intended effects cannot be obtained. Where the amount of Mn is over 0.20%, workability in plastic working is degraded. Accordingly, the contained amount of Mn is set to 0.05% or more and 0.20% or less in the preferred magnesium alloy. The preferable contained amount of Mn is 0.10% or more and 0.20% or less.

Unavoidable Impurities

For the magnesium alloy, it is preferable that the contained amount of the unavoidable impurities is also controlled. Since Fe, Ni, Co, and Cu enhance corrosion of the magnesium alloy, it is preferable to control an amount of each of these elements to be less than 10 ppm, more preferably 5 ppm or less, and still more preferably the magnesium alloy is essentially free of these elements. Preferably, the total amount of unavoidable impurities is controlled to be 30 ppm or less, more preferably 10 ppm or less. Further, it is preferable that the magnesium alloy is essentially free of rare earth and aluminum. Here, a state where the contained amount of a target substance is less than 1 ppm is recognized as "essentially free" of that substance. The amount of unavoidable impurities may be determined, for example, by ICP emission spectrometry.

Production of Magnesium Alloy

The above magnesium alloy can be produced, in accordance with usual production method of magnesium alloys, throwing ground metals or alloys of Mg, Zn, Zr, and Mn into a crucible, melting the ground metals and/or alloys in the crucible at a temperature of 650 to 800° C. to form a molten alloy, and casting the molten alloy. Where necessary, the cast alloy is subjected to solution heat treatment. Rare earth element-free (and aluminum-free) metals are used as the ground metals. It is possible to suppress the amounts of Fe, Ni, Co, and Cu in the impurities by the use of ground metals with high purity. Fe, Ni, and Co in the impurities of molten alloy may be removed by iron-extraction treatment after it has been melted. In addition or alternatively, it is possible to use ground metals produced by distillation refining.

Metallic Morphology and Mechanical Property

The magnesium alloy may have, in terms of grain size distribution, a fine and uniform structure having an average crystal grain size of 1.0 to 3.0 µm (for example, 1.0 to 2.0 µm), and a standard deviation of 0.7 µm or less (for example, 0.5 to 0.7 µm), by means of controlling the composition of the alloy and controlling the method for manufacturing. The standard deviation is preferably 0.65 µm or less. The fine precipitate including Zr may have a grain size of less than 500 nm, preferably less than 100 nm. The matrix excluding the Zr precipitates is preferably a total solid solution of the Mg—Zn—Mn ternary alloy.

The alloy may have mechanical properties, as measured by JIS Z2241, such as a tensile strength of 230 to 380 MPa (for example, 250 to 300 MPa), a proof strength of 145 to 220 MPa, and a fracture elongation of 15 to 50% (for example, 25 to 40%). Here, the tensile strength preferably exceeds 280 MPa. The fracture elongation preferably exceeds 30%.

Shape of Magnesium Alloy

The magnesium alloy may have a wheel shape, a plate shape, a rod shape, a pipe shape, a band shape, a wire shape, a ring shape, or a combinational shape of the above at least one shape. On the magnesium alloy having a shape selected in view of its use, the above-described first layer and second layer may be formed.

Formation of Magnesium Fluoride Layer

The surface of the magnesium alloy (core structure) having a predetermined shape is subjected to fluorination treatment. As far as a $MgF_2$ layer can be formed, the conditions for fluorination treatment are not specifically limited. For example, the magnesium alloy can be immersed into a treating solution, such as a hydrofluoric-acid aqueous solution. It is preferred to immerse the magnesium alloy with shake, for example, at 50 to 200 ppm, preferably 80 to 150 ppm. Then, the magnesium alloy on which $MgF_2$ layer is formed is taken out of the solution, followed by washing sufficiently with cleaning fluid (for example, acetone aqueous solution), for example, by ultrasonic cleaning. Where the washed magnesium alloy is subjected to drying, it is preferred that the magnesium alloy is dried at 50 to 60° C. for 24 hours or longer under vacuum.

Structure of Magnesium Fluoride Layer

The magnesium fluoride layer comprises mainly magnesium fluoride. For example, magnesium fluoride layer may comprise mainly $MgF_2$ in a concentration of 90% or more. Further, oxides such as $MgO$ and $Mg(OH)_2$ and hydroxides may be contained as auxiliary components. It should be noted that the magnesium fluoride layer may contain oxides and hydroxides of metals other than magnesium that constitute the medical device for the above purpose.

Layer Thickness of Magnesium Fluoride Layer

The layer thickness of the magnesium fluoride layer may be preferably 0.5 µm or more in view of anticorrosion properties, and 3 µm or less in view of deformation followability.

Formation of Parylene Layer

According to the present invention, a second anticorrosion layer made of parylene is formed on the first anticorrosion layer. The parylene layer may have a thickness of 0.05 to 1 µm, preferably 0.08 to 0.8 µm, so that the corrosion resistance of the magnesium alloy can be significantly improved, without impairing the bioabsorbable property. Where the thickness of the second anticorrosion layer is too thin, the anticorrosion effect is inclined to be insufficient, whereas if the thickness thereof is too thick, the bioabsorbable property is inclined to be impaired.

Parylene collectively refers to paraxylylenes and derivatives thereof. Examples of parylenes may include: a parylene N having no functional group in the aromatic ring [the following formula (1)], a parylene C in which one of the hydrogens in the aromatic ring is substituted with chlorine [the following formula (2)], a parylene M in which one of the hydrogens in the aromatic ring is substituted with a methyl group [the following formula (3)], a parylene F in which one of the methylene groups of the parylene M is fluorinated [the following formula (4)], a parylene D in which hydrogens at the 2,5-positions of the aromatic ring of the parylene N are replaced by chlorine [the following formula (5)], and a parylene HT in which both the methylene groups of the parylene N are fluorinated [the following formula (6)]. These parylenes are commercially available; for example, a parylene N and a parylene C can be obtained from Dai San Kasei Co., Ltd.

[Chem. 2]

(1)

(2)

(3)

(4)

(5)

(6)

According to the present invention, a thin parylene layer may have a thickness of 0.05 to 1 μm formed on the magnesium fluoride layer. Because of this configuration, the corrosion resistance of the Mg alloy can be significantly improved, without impairing the bioabsorbable property. Where the thickness of the parylene layer is too thin, the anticorrosion effect is inclined to be insufficient, whereas if the thickness thereof is too thick, the bioabsorbable property is inclined to be impaired.

Biomaterial Layer

In the present invention, a biomaterial layer such as biodegradable polymer, protein, or calcium phosphate may be formed on the entire surface or a part of the surface of the parylene layer. As the biodegradable polymer, there may be mentioned polyesters etc., and examples of the biodegradable polymer may include a poly(L-lactic acid) (PLLA), a poly(D,L-lactic acid) (PDLLA), a polylactic acid-glycolic acid (PLGA), a polyglycolic acid (PGA), a polycaprolactone (PCL), a poly(lactic acid-ε-caprolactone) (PLCL), a polyglycolic acid-ε-caprolactone (PGCL), a poly(p-dioxanon), a poly(glycolic acid-trimethylenecarbonate), a poly(β-hydroxybutyric acid), and the like. Examples of the protein may include collagen, gelatin, fibroin, and the like. Examples of the calcium phosphate may include hydroxyapatite, β-tricalcium phosphate, octacalcium phosphate.

Drug

Depending on the therapeutic purpose in which the non-luminal implant according to the present invention is used, the biomaterial layer may contain a drug(s).

Medical Use

The obtained non-luminal implant may be used for patient care as an alloy for orthopedic implants, an alloy for oral surgery implants, an alloy for plastic surgery implants, or an alloy for cerebral surgery. Specific examples may include alloys for sutures such as clips, staplers, wires and sewing needles, and alloys for osteosynthesis members such as bone pins, bone screws and suture anchors

EXAMPLES

Production Examples 1 and 2 of Magnesium Alloy

High purity ground metals of Mg, Zn, Mn, and Zr were prepared as raw materials. Respective components were weighted so as to constitute the component concentration shown in Table 1, and were thrown into a crucible, and were molten at 730° C. Each melt was stirred in the crucible, and was cast to form an ingot. Each of the thus-obtained magnesium alloys of Production Examples 1 and 2 was made to have a blending ratio of the main component within the range of the present invention. Rare earth elements and aluminum were not contained in the raw materials even as unavoidable impurities. Magnesium was provided from a magnesium ground metal of purity level of 99.99% with low concentration of impurity Cu, and molten alloy in the crucible were subjected to iron-extraction treatment so as to remove iron and nickel from the molten alloy. Impurity concentrations of the thus obtained samples were measured using an ICP emission spectrometer (AGILENT 720 ICP-OES made by Agilent Technologies). The components of Production Example 1 and Production Example 2 are shown in Table 1. In each of Production Examples 1 and 2, respective concentrations of Fe, Ni, and Cu were not more than 8 ppm (with regard to Ni and Cu, not more than 3 ppm), and Al and rare earth elements were not detected. Concentration of Co was also below measurable limits. The concentration of the total amount of impurity is 11 to 12 ppm.

TABLE 1

| | Component Concentration (% by mass) | | | | Impurity Concentration (ppm) | | | |
|---|---|---|---|---|---|---|---|---|
| | Mg | Zn | Mn | Zr | Fe | Ni | Cu | Sum |
| Production Example 1 | remnant | 1.86 | 0.14 | 0.12 | 5 | 3 | 3 | 11 |
| Production Example 2 | remnant | 0.95 | 0.11 | 0.24 | 8 | 3 | 1 | 12 |

Measurement of Mechanical Properties

The alloys of the Production Examples were respectively worked to round rods by heat extrusion, and each rod was subjected to measurements of tensile strength, proof stress, and fracture elongation according to JIS Z2241. The results are shown in Table 2.

TABLE 2

| | Tensile strength (MPa) | Proof stress (MPa) | Fracture elongation (%) | Average crystal grain size (μm) | Standard Deviation (μm) |
|---|---|---|---|---|---|
| Production Example 1 | 288 | 213 | 38 | 1.97 | 0.62 |
| Production Example 2 | 297 | 217 | 27 | 1.97 | 0.63 |

Production Example 3

High purity ground metals of Mg, Zn, Mn, and Zr were prepared as raw materials. Respective components were weighted so as to constitute the component concentration shown below, and were thrown into a crucible, and were molten at 730° C. Each melt was stirred in the crucible, and was cast to form an ingot. Rare earth elements and aluminum were not contained in the raw materials even as unavoidable impurities.

Magnesium was provided from a magnesium ground metal of purity level of 99.99% with low concentration of impurity Cu, and molten alloy in the crucible were subjected to iron-extraction treatment so as to remove iron and nickel from the molten alloy.

Impurity concentrations of the thus obtained ingot were measured using an ICP emission spectrometer (AGILENT 720 ICP-OES made by Agilent Technologies).

Component concentration (w %) of the obtained ingot was as follows, and the ingot did not contain aluminum and rare earths.

Mg Remnant, Zn 1.5%, Mn 0.4%, Zr 0.4%, and the ingot contained Fe, Ni, Co and Cu as unavoidable impurities at the following concentrations.

Fe 5 ppm, Ni 5 ppm, Co ND (below detection limits), Cu 1 ppm.

Production of Magnesium Plate

Figure 2:
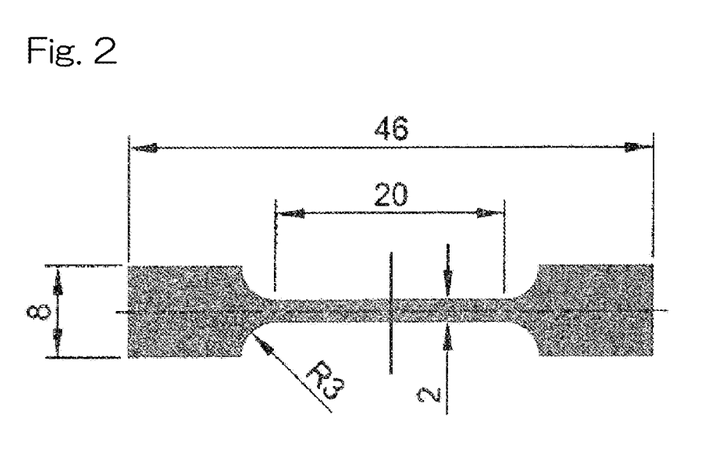
FIG. 2 is a schematic diagram illustrating a sample shape used in Example which shows an example of an implant for a non-luminal region according to an embodiment of the present invention.

The magnesium alloy ingot produced in Production Example 3 was processed into a shape (thickness: 1 mm) shown in FIG. 2 (the dimension shown in FIG. 2 is mm) so as to form a magnesium alloy substrate A.

The magnesium alloy ingot produced by Production Example 3 was processed into a disc shape (diameter 50 mm×thickness 1 mm) so as to form a magnesium alloy substrate B.

Electrolytic Polishing of Magnesium Alloy Substrate

Oxide particles deposited on the surface of the obtained magnesium alloy substrate was removed by acid solution.

The magnesium alloy substrate was then immersed in the electrolytic solution as a positive electrode, with placing metal plates as negative electrode, and these electrodes were electrically connected through a direct-current power supply. In such a state, a voltage was applied, whereby the magnesium alloy substrate of the positive electrode was mirror polished so as to obtain a smooth surface. In order to stabilize the mucous layer while applying the voltage, the electrolytic solution was agitated. In such a manner, the temperature was kept constant. Moreover, in order to suppress generation of air bubbles on the negative electrode, applying and cutting of the voltage was appropriately repeated. If the air bubbles are liberated from the negative electrode and deposited on the magnesium alloy substrate, defect on surface accuracy will arise.

From the obtained magnesium alloy substrate with the mirror-surface, the samples illustrated in the following Examples and Comparative Examples were prepared.

Evaluation of Weight Residual Ratio and Tensile Strength Residual Ratio

Each of the obtained samples was immersed in the simulated plasma solution (EMEM+10% FBS), and was shaken at 100 rpm with keeping immersion at 37° C. under 5% $CO_2$ atmosphere. After 28 days of immersion, the sample was taken out of the solution and ultrasonically cleaned with chromic acid so as to completely remove corrosion products such as magnesium hydroxide, and the weight residual ratio before and after immersion was evaluated (n=5).

On another front, the obtained sample was shaken with keeping immersion in the same manner, and after 28 days of immersion, the sample was taken out of the solution and cleaned so as to remove corrosion products, and the sample was chucked in a tensile tester and subjected to a tensile test at a crosshead speed of 5 mm/min. In such a manner, the tensile strength residual ratio before and after immersion was evaluated (n=5).

Example 1

The magnesium alloy substrate A with the mirror surface was immersed in a 27M aqueous hydrofluoric acid solution and shaken at 100 rpm. The sample taken out of the solution after 24 hours was thoroughly ultrasonically cleaned with water and acetone, and then dried at 60° C. under reduced pressure for 24 hours. Accordingly, a sample having a magnesium fluoride layer (thickness 1 μm) was obtained. A parylene layer C with a thickness of 500 nm was further formed on the sample by CVD method so as to obtain a sample having a parylene layer on a magnesium fluoride layer.

Example 2

A sample obtained in the same manner as in Example 1 was immersed in a 1% polylactic acid solution for 3 minutes. The 1% polylactic acid solution was prepared by dissolving 1% polylactic acid in THF. The sample taken out of the solution was dried at 60° C. under reduced pressure for 24 hours. In such a manner, a sample having a magnesium fluoride layer, a parylene layer, and a polylactic acid layer in this order was obtained.

Comparative Example 1

The magnesium alloy substrate A with the mirror surface was immersed in a 27 M aqueous hydrofluoric acid solution and shaken at 100 rpm. The sample taken out of the solution after 24 hours of immersion was thoroughly ultrasonically cleaned with water and acetone, and then dried at 60° C. under reduced pressure for 24 hours. Accordingly, a sample having a magnesium fluoride layer (thickness 1 μm) was obtained.

Comparative Example 2

The magnesium alloy substrate A with the mirror surface (unfluorinated) was subjected to CVD method so as to obtain a sample having a parylene layer C at a thickness of 500 nm.

Comparative Example 3

A sample obtained in the same manner as in Comparative Example 2 was immersed in a 1% polylactic acid solution for 3 minutes. The 1% polylactic acid solution was prepared by dissolving 1% polylactic acid in THF. The sample taken out of the solution was dried at 60° C. under reduced pressure for 24 hours. In such a manner, a sample having a polylactic acid layer on a parylene layer was obtained.

Table 3 shows the results of measuring the weight residual ratio of the samples; Table 4 shows the results of measuring the tensile strength residual ratio of the samples. It should be noted that the weight of the sample before immersion was 0.36±0.1 g, and the tensile strength of the sample before immersion was 310±10 MPa.

TABLE 3

Weight residual ratio (%) before and after immersion

| | Before immersion | After immersion |
| --- | --- | --- |
| Example 1 | 100 | 99.3 ± 0.7 |
| Example 2 | 100 | 98.4 ± 1.1 |
| Comparative Example 1 | 100 | 94.8 ± 1.2 |
| Comparative Example 2 | 100 | 89.5 ± 2.6 |
| Comparative Example 3 | 100 | 89.9 ± 3.1 |

TABLE 4

Tensile strength residual ratio (%) before and after immersion

| | Before immersion | After immersion |
| --- | --- | --- |
| Example 1 | 100 | 96.0 ± 1.4 |
| Example 2 | 100 | 96.3 ± 2.2 |
| Comparative Example 1 | 100 | 87.8 ± 2.9 |
| Comparative Example 2 | 100 | 81.5 ± 4.0 |
| Comparative Example 3 | 100 | 79.3 ± 3.7 |

The samples according to the present invention (Example 1 and Example 2) had significantly smaller changes in weight and tensile strength compared to the sample without the parylene layer (Comparative Example 1) and the samples without the magnesium fluoride layer (Comparative Examples 2 and 3), suggesting that an excellent anticorrosion effect can be obtained by the double layer structure of the magnesium fluoride layer and the parylene layer.

Inflammatory Evaluation Caused by Placement of Implant Under Mouse Skin

A sample having excellent anticorrosive properties can suppress an inflammatory reaction related to corrosion in a living tissue. Accordingly, the anticorrosion property of the sample can be comprehended by means of evaluating the inflammation of the tissue.

The obtained test samples were implanted subcutaneously (under the skin) in the back of the mouse (two test samples per mouse), and on the 60$^{th}$ day, the inflammation of the tissue was evaluated in accordance with the following 4 scores (n=5).

| Class | Criteria for evaluation |
|---|---|
| 0 | Inflammatory cells are not detected around the strut. |
| 1 | A few inflammatory cells were detected around the strut. |
| 2 | Inflammatory cells were detected at a covering amount of 50% or more in the area around the strut. |
| 3 | Entire surroundings of the strut was covered by inflammatory cells. |

Example 3

The magnesium alloy substrate B with the mirror surface was immersed in a 27M aqueous hydrofluoric acid solution and shaken at 100 rpm. The sample taken out of the solution after 24 hours was thoroughly ultrasonically cleaned with water and acetone, and then dried at 60° C. under reduced pressure for 24 hours. Accordingly, a sample having a magnesium fluoride layer (thickness 1 μm) was obtained. A parylene layer C with a thickness of 500 nm was further formed on the sample by CVD method so as to obtain a sample having a parylene layer on a magnesium fluoride layer.

Example 4

A sample obtained in the same manner as in Example 3 was immersed in a 1% polylactic acid solution for 3 minutes. The 1% polylactic acid solution was prepared by dissolving 1% polylactic acid in THE. The sample taken out of the solution was dried at 60° C. under reduced pressure for 24 hours. In such a manner, a sample having a polylactic acid layer on a parylene layer on a magnesium fluoride layer was obtained.

Comparative Example 4

The magnesium alloy substrate B with the mirror surface was immersed in a 27M aqueous hydrofluoric acid solution and shaken at 100 rpm. The sample taken out of the solution after 24 hours was thoroughly ultrasonically cleaned with water and acetone, and then dried at 60° C. under reduced pressure for 24 hours. In such a manner, a sample having a magnesium fluoride layer (thickness 1 μm) was obtained.

Comparative Example 5

The magnesium alloy substrate B with the mirror surface (unfluorinated) was treated with parylene C by CVD method so as to obtain a sample having a parylene layer C in a thickness of 500 nm.

Comparative Example 6

A sample obtained in the same manner as in Comparative Example 5 was immersed in a 1% polylactic acid solution for 3 minutes. The 1% polylactic acid solution was prepared by dissolving 1% polylactic acid in THF. The sample taken out of the solution was dried at 60° C. under reduced pressure for 24 hours. In such a manner, a sample having a polylactic acid layer on a parylene layer was obtained.

Inflammatory evaluations of the samples obtained in Examples 3, 4 and Comparative Examples 4 to 6 were illustrated in Table 5.

TABLE 5

Inflammatory score of mouse on the 60$^{th}$ day of the subcutaneous implant.

| | No. 1 | No. 2 | No. 3 | No. 4 | No. 5 | Average |
|---|---|---|---|---|---|---|
| Example 3 | 1 | 1 | 0 | 1 | 1 | 0.8 ± 0.4 |
| Example 4 | 1 | 1 | 1 | 1 | 1 | 1.0 ± 0.0 |
| Com. Ex. 4 | 1 | 2 | 2 | 2 | 7 | 1.8 ± 0.4 |
| Com. Ex. 5 | 1 | 2 | 2 | 2 | 2 | 1.8 ± 0.4 |
| Com. Ex. 6 | 1 | 2 | 2 | 2 | 2 | 1.8 ± 0.4 |

Note:
No. 1 to No. 5 indicate Sample No.

The samples according to the present invention (Example 3 and Example 4) showed significantly smaller inflammatory scores of the tissues compared to the sample without the parylene layer (Comparative Example 4) and the samples without the magnesium fluoride layer (Comparative Examples 5 and 6), suggesting that an excellent anticorrosion effect can be obtained by the double layer structure of the magnesium fluoride layer and the parylene layer.

INDUSTRIAL APPLICABILITY

The present invention provides a non-luminal implant including: a magnesium fluoride layer effective in delaying the decrease in mechanical strength associated with accelerated corrosion of the magnesium alloy structure; and a parylene layer formed on the magnesium fluoride layer. Since such an implant can contribute to the development on medical technology, it has extremely high industrial potential.

Although the present invention has been fully described in connection with the preferred examples thereof with reference to the accompanying drawings, those skilled in the art can easily assume various changes and modifications within a self-evident range by looking at the present specification and the drawings. Accordingly, such changes and modifications are to be construed as being within the scope of the invention from the claims.

REFERENCE NUMERALS a . . . Mg alloy
b . . . a first covering layer (magnesium fluoride layer)
c . . . a second covering layer (parylene layer)

What is claimed is:
1. A bioabsorbable implant for non-luminal region comprising:
a core structure comprising a magnesium alloy having a predetermined shape, the magnesium alloy comprising, in % by mass,
from 0.95 to 2.00% of zinc,
from 0.05% to less than 0.30% of zirconium,
from 0.05 to 0.20% of manganese, and
the balance consisting of magnesium and unavoidable impurities,
wherein the magnesium alloy is free from rare elements and aluminum, and
wherein the total amount of unavoidable impurities being controlled to be 10 ppm or less;

a first corrosion-resistant layer containing a magnesium fluoride layer as a main component formed on the core structure via fluorination of a surface of the magnesium alloy; and a second corrosion-resistant layer containing a parylene formed on the magnesium fluoride layer.

2. The implant for non-luminal region according to claim 1, wherein the magnesium alloy has an average crystal grain size of 1.0 to 3.0 μm and a standard deviation of grain size distribution of 0.7 μm or less.

3. The implant for non-luminal region according to claim 1, wherein the magnesium alloy has a wheel shape, a plate shape, a rod shape, a pipe shape, a band shape, a wire shape, a ring shape, or a combination of at least one shape thereof.

4. The implant for non-luminal region according to claim 1, wherein the implant for non-luminal region is for orthopedic use, oral surgical use, plastic surgical use, or cerebral surgical use.

5. The implant for non-luminal region according to claim 1, wherein the implant for non-luminal region is used as (1) an implant for suture instruments such as a clip, a stapler, a wire, and a surgical needle, or (2) an implant as bone junction members such as a bone pin, a bone screw, a suture anchor.

6. The implant for non-luminal region according to claim 1, wherein the magnesium fluoride layer has a layer thickness of 0.5 to 1.5 μm.

7. The implant for non-luminal region according to claim 1, wherein the parylene layer comprises a parylene N (chemical formula 1 below), a parylene C (chemical formula 2 below), a parylene M (chemical formula 3 below), a parylene F (chemical formula 4 below), a parylene D (chemical formula 5 below), or a parylene HT (chemical formula 6 below),

(1)

(2)

(3)

(4)

(5)

(6)

8. The implant for non-luminal region according to claim 1, wherein the parylene layer has a layer thickness of 0.05 to 1 μm.

9. The implant for non-luminal region according to claim 1, wherein a biodegradable polymer layer comprising a biomaterial selected from the group consisting of a biodegradable polymer, a protein, and a calcium phosphate layer is formed on at least a part of the surface of the parylene layer.

10. A method of producing a non-luminal implant comprising (1) a magnesium fluoride layer on a surface of a magnesium alloy and (2) a parylene layer on the magnesium fluoride layer, the magnesium alloy comprising, in % by mass, from 0.95 to 2.00% of zinc,
from 0.05% to less than 0.30% of zirconium,
from 0.05 to 0.20% of manganese, and
the balance consisting of magnesium and unavoidable impurities,
  wherein the magnesium alloy is free from rare elements and aluminum, and
  wherein the total amount of unavoidable impurities being controlled to be 10 ppm or less,
the method comprising:
  (1) subjecting a surface of a magnesium alloy having a predetermined shape to fluorination treatment to form a magnesium fluoride layer on the surface of the magnesium alloy, and
  (2) subjecting the magnesium fluoride layer vapor deposition coating of poly-para-xylylene resin to form a parylene layer.

* * * * *